United States Patent [19]

Criscuolo et al.

[11] Patent Number: 5,112,617

[45] Date of Patent: May 12, 1992

[54] METHOD FOR CONTROLLING COLD SYMPTOMS

[76] Inventors: Pascual A. Criscuolo, Pueyrredon 2488, Piso 11°"A"; Arnaldo J. Caldirola, Rosetti 236, both of Capital Federal, Argentina

[21] Appl. No.: 487,415

[22] Filed: Mar. 1, 1990

[51] Int. Cl.$^5$ ............... A01N 25/04; A61K 9/10; A61K 31/075; A61K 31/045

[52] U.S. Cl. .................... 424/434; 424/400; 424/435; 424/195.1; 514/714; 514/724; 514/937

[58] Field of Search ............... 514/827, 828, 937, 969, 514/714, 724; 435/843, 871, 873, 885, 884; 424/400, 404, 405, 195.1, 434, 435

[56] References Cited

U.S. PATENT DOCUMENTS 4,044,120  8/1977  Rowsell et al. ............... 514/588
4,383,985  5/1983  Dubash et al. ............... 424/78
4,557,898 12/1985  Greene et al. ............... 514/714
4,900,721  2/1990  Bansemir et al. ............... 514/714

OTHER PUBLICATIONS

Robbins, Stanley L., Pathologic Basis of Disease, 3rd Ed., 1984, p. 763.

Primary Examiner—Thurman K. Page
Assistant Examiner—Carlos Azpuru
Attorney, Agent, or Firm—Scully Scott Murphy & Presser

[57] ABSTRACT

A composition for control of cold symptoms comprising 80-90% of 8% strength hydrogen peroxide, 3-7% hammermelis water 3-7% orange flower water, 0.1-0.5% magnesium carbonate, 0.05-0.15% almond essence and 3-6% ethyl alcohol. The composition is applied topically to the nasal mucous whereafter reduction in mucous production is realized.

4 Claims, No Drawings

METHOD FOR CONTROLLING COLD SYMPTOMS

BACKGROUND OF THE INVENTION

Among illnesses affecting man, the chill or common cold constitutes one of the most widespread, if not the most widespread, in the world.

While it does not in itself constitute, generally speaking, a dangerous illness, if [sic] it is dangerous in respect of the concomitant complications which can arise in the patient, owing to the fact that it is the means of entry for causative microorganisms of other illnesses which are serious, and even in some cases fatal, especially in the case of elderly patients or babies in the first few months of life, as well as during their first few years, where weakening of the body's natural organic defences can bring the patient to the point where there is a genuine danger to his or her life.

Moreover, from the standpoint of the economy and the workforce, the cold is also a cause of great difficulties, due to the reduction in hours worked through the absence of sick personnel.

The features described above constitute but a small part of the manifold difficulties caused by the cold in the life of man, for which reason it is becoming essential to find a means which makes it possible, at least, to control said illness in the patient.

The capacity of the cold virus to withstand the action of the countless medicaments existing in the world for its cure, all of which have failed, to a greater or lesser extent, to achieve total defeat of this illness, is also known.

Accordingly, the provision of a composition or medicament which would enable the effects of the cold to be controlled in a sick individual constitutes a substantial contribution to the arsenal of the products or drugs used for combating this illness.

SUMMARY OF THE INVENTION

The subject of the present invention is a composition which enables control to be exerted over the cold symptoms, acting locally on the nasal cavities, producing a rapid reduction in nasal secretion. The active principles of this composition possess a marked bactericidal action, acting as a barrier to the subsequent entry of microorganisms into the patient's body, thereby facilitating a more rapid recovery on the patient's part. The administration of this composition to the patient does not require special precautions.

The composition for control of the cold symptoms which is the subject of this invention consists of a mixture of 8% strength hydrogen peroxide, Hamamelis water, orange flower water, magnesium carbonate in a very pure suspension, almond essence and ethyl alcohol.

DESCRIPTION OF THE PREFERRED EMBODIMENTS

More specifically, the subject of the present invention is a composition for control of the cold symptoms, composed of a mixture of 80 to 90% of 8% strength hydrogen peroxide, 3 to 7% of Hamamelis water, 3 to 7% of orange flower water, 0.1 to 0.5% of magnesium carbonate in very fine suspension, 0.05 to 0.15% of almond essence and 3 to 6% of ethyl alcohol, where the value of the percentage of each component is to be selected in such a way that the sum total amounts to 100%.

In said composition, the hydrogen peroxide, which possesses disinfectant and antiseptic properties, acts as a bactericide and controlling agent of the cold, preventing spread of the causative virus of the illness.

Hamamelis water constitutes an astringent lotion which protects the nasal and buccal mucosae, exerting, moreover, a soothing action thereon.

Orange flower water is prepared from orange flowers and possesses a sedative action. In the composition of the present invention, it acts in a similar manner to the Hamamelis water.

Magnesium carbonate, which occurs in the composition in the form of a very finely divided stable suspension, acts by forming a protective film on the nasal mucosa.

Almond essence functions as a flavoring for the composition which is the subject of the invention.

Finally, ethyl alcohol exerts an antiseptic action on the nasal mucosa.

The preparation of the composition for control of the cold symptoms, which is the subject of the invention, is carried out by simple mixing of the components at room temperature, no preset order being observed as regards the addition of the components to the mixture.

EXAMPLE

A specific example of a composition according to the invention for control of the cold symptoms is given below:

| | |
|---|---|
| Hydrogen peroxide, 8% strength | 85.0 ml |
| Hamamelis water | 5.0 ml |
| Orange flower water | 5.0 ml |
| Magnesium carbonate (very fine suspension) | 0.3 g |
| Almond essence | 0.1 ml |
| Ethyl alcohol | 4.6 ml | for a total quantity of composition of 100 ml.

This composition acts on cold symptoms of any origin, the nasal cavities being moistened there with three or four times daily.

The application is carried out by placing a drop of the composition on one finger of the hand and rubbing the nasal mucosa gently therewith.

Three pre- and post-treatment trials were carried out, for the purpose of determining, in different patients, the reduction in the number of colonies of microorganisms present in the nasal mucosa thereof.

PATIENT NO. 1

Pretreatment

By direct microscopic examination, no particulate matter was observed. By Gram Nicolle staining, an abundance of Gram-negative coccobacilli was observed. By means of culturing, *Proteus mirabilis* 100% was isolated. A colony count gave a value of 270,000 colonies isolated, a 1:100 dilution being performed.

Post-treatment

By means of direct microscopic examination, no particulate matter was observed. By Gram Nicolle staining, an average quantity of Gram-negative coccobacilli was observed. By means of culturing, *Proteus mirabilis* 100% was isolated. A colony count gave a value of 148,000 with a dilution of 1:100, which constitutes an appreciable decrease in the number of colonies present in the nasal mucosa analyzed.

PATIENT NO. 2

Pretreatment

By direct microscopic examination, an average quantity of cells and leukocytes was observed. By means of Gram Nicolle staining, an average quantity of Gram-positive cocci and Gram-negative diplococci was detected. From a culture of the nasal mucosa sample, *Streptococcus viridans* 50% was isolated. A colony count gave a value of 100,000 colonies isolated.

Post-treatment

Direct microscopic examination enabled an average quantity of cells and leukocytes to be detected. Gram Nicolle staining enabled an average quantity of Gram-positive cocci and Gram-negative diplococci to be observed. By means of culturing the sample, *Staphilococcus* [sic] *epidermidis* 40%, *Streptococcus viridans* 40% and *Neisseria specifica* 20% were isolated. A colony count gave a total value of 40,000 colonies, which signifies a noteworthy reduction in the number of the latter.

PATIENT NO. 3

Pretreatment

By means of a direct microscopic examination, an average quantity of cells and leukocytes, as well as of pyocytes and fibrin, was observed. By Gram Nicolle staining, an abundance of Gram-positive cocci and bacilli and Gram-negative diplococci was detected. From a culture of the sample, *Staphylococcus epidermidis* 40%, *Neisseria specifica* 40% and *Corynebacterium specifica* 20% were isolated. A colony count gave a value of 100,000 colonies.

Post-treatment

Direct microscopic examination revealed the presence of an average quantity of cells and few leukocytes. By means of Gram Nicolle staining, an average quantity of Gram-positive and -negative cocci was detected. Culturing of the sample enabled *Staphylococcus epidermidis* 70% and *Neisseria specifica* 30% to be isolated. A colony count gave a value of only 10,000 colonies, that is to say around 10% of the value found in the sample taken before the treatment.

As may be observed from the above trials, treatment with the composition which is the subject of the invention has given positive results for control of the cold symptoms, irrespective of its origin.

We claim:

1. A method for the reduction of nasal secretion and congestion in upper respiratory cavities in a human being comprising:
    applying to a nasal mucosa of a human being an effective dosage, in liquid form, for the reduction of nasal secretion and congestion in upper respiratory cavities of a human being of a mixture of 80 to 90% of 8% strength hydrogen peroxide, 3 to 7% of Hamamelis water, 3 to 7% of orange flower water, 0.1 to 0.5% of magnesium carbonate in very fine suspension, 0.05 to 0.15% of almond essence and 3 to 6% of ethyl alcohol; where the value of the percentage of each component is to be selected in such a way that the sum total amounts to 100%.

2. A method according to claim 1 wherein the mixture comprises:
    85 ml of 8% strength hydrogen peroxide, 5 ml of Hamamelis water, 5 ml of orange flower water, 0.3 g of magnesium carbonate in very fine suspension, 0.1 ml of almond essence and 4.6 ml of ethyl alcohol, for a total quantity of composition of 100 ml.

3. A method for the reduction of nasal secretion and congestion in upper respiratory cavities in a human being comprising:
    applying to a nasal mucosa of a human being an effective dosage, in liquid form, for the reduction of nasal secretion in upper respiratory cavities in a human being of a mixture of 80 to 90% of 8% strength hydrogen peroxide, 3 to 7% of Hamamelis water, 3 to 7% of orange flower water, 0.1 to 0.5% of magnesium carbonate in very fine suspension, 0.05 to 0.15% of almond essence and 3 to 6% of ethyl alcohol; where the value of the percentage of each component is to be selected in such a way that the sum total amounts to 100%, and wherein the reduction of nasal secretion is due to the inhibition of the growth of *Proteus mirabilis, Streptococcus viridans, Staphylococcus epidermidis, Neisseria specifica* or *Corynebacterium specifica.*

4. A method for neutralizing or inhibiting the growth of cold pathogens in a human being comprising:
    applying to a nasal mucosa of a human being an effective dosage, in liquid form, for neutralizing or inhibiting the growth of *Proteus mirabilis, Streptococcus viridans, Staphylococcus epidermidis, Neisseria specifica* or *Corynebacterium specifica* of a mixture of 80 to 90% of 8% strength hydrogen peroxide, 3 to 7% of Hamamelis water, 3 to 7% of orange flower water, 0.1 to 0.5% of magnesium carbonate in very fine suspension, 0.05 to 0.15% of almond essence and 3 to 6% of ethyl alcohol; where the value of the percentage of each component is to be selected in such a way that the sum total amounts 100%.

* * * * *